United States Patent [19]

Svendsen

[11] 4,016,042
[45] Apr. 5, 1977

[54] SUBSTRATE FOR THE QUANTITATIVE DETERMINATION OF ENZYMES

[75] Inventor: Lars Gundro Svendsen, Reinach, Switzerland

[73] Assignee: Pentapharm A.G., Basel, Switzerland

[22] Filed: June 30, 1975

[21] Appl. No.: 592,023

[30] Foreign Application Priority Data

July 2, 1974 Switzerland .................. 9210/74
May 9, 1975 Switzerland .................. 6088/75

[52] U.S. Cl. .................. 195/103.5 R; 195/99; 260/112.5 R
[51] Int. Cl.$^2$ .................. G01N 31/14
[58] Field of Search .................. 195/103.5 R, 99; 260/112.5 R, 112.5

[56] References Cited

UNITED STATES PATENTS 3,884,896  5/1975  Blomback et al. .......... 195/103.5 R
3,886,136  5/1975  Claeson et al. ............ 260/112.5 R

OTHER PUBLICATIONS

Ontjes et al. "Radio Chemical Assay for Renin Utilizing on Synthetic Insoluble Substrate" Anal. Biochem. 45, pp. 374–386 (1972).

Primary Examiner—David M. Naff
Assistant Examiner—C. A. Fan
Attorney, Agent, or Firm—Pennie & Edmonds

[57] ABSTRACT

A synthetic substrate having the structure $$R^1 - Pro - X - Y - NH - R^2,$$

wherein $R^1$ is a blocking group, $-NH-R^2$ is a chromogenic or fluorescent group, X represents a phenylalanyl, β-cyclohexylanyl, phenylglycyl or tyrosyl group, and Y represents a protonized arginyl or lysyl group, is disclosed. This substrate is useful for the quantitative determination of proteolytic enzymes of class E.C. 3.4.4., except thrombin and thrombin-like enzymes.

12 Claims, 3 Drawing Figures

Proteinase Inhibitor Units (Obtained from Lung)

Time in Minutes at which Blood Samples were Taken after Scalding of the Rat

SUBSTRATE FOR THE QUANTITATIVE DETERMINATION OF ENZYMES

BACKGROUND OF THE INVENTION

The present invention relates to synthetic reagents or substrates which are used for the quantitative determination of proteolytic enzymes. More particlarly, the invention relates to a synthetic chromogenic or fluorescent tripeptidic substrate which is useful as a reagent for the quantitative determination of proteolytic enzymes of class E.C. 3.4.4., which split peptide chains on the carboxyl side of arginine as well as lysine, except thrombin and thrombin-like enzymes, in human and mammal body fluids as well as in vegetable and animal cell extracts and in glandular venoms of cold-blooded animals such as snakes.

The quantitative determination of kallikrein, a proteolytic enzyme which occurs in human and mammal body fluids (e.g. blood plasma) and organs (e.g. pancreas) and which has a vasodilatatory action, is carried out, on the one hand, by biological methods and, on the other hand, by enzymatic methods. The biological methods consist in measuring the changes caused by kallikrein in the carotis pressure of narcotized dogs, or in determining kallikrein on isolated guinea-pig intestine in tyrode solution by measuring the quantity of kinine released from kininase-free kininogen solutions (cf. E.K. FREY et al., "Das Kallikrein-Kinin-System und seine Inhibitoren", Ferdinand Enke Verlag, Stuttgart, 1968, p. 11 and 12). These biological methods have a major disadvantage because they require the cumbersome and expensive use of test animals. In order to overcome this difficulty, the so-called enzymatic determination methods were developed. These methods make use of the esterolytic action exerted on certain ester substrates by kallikrein. Substrates of this type include e.g. $N^\alpha$-benzoyl-L-arginine ethyl ester which is split by kallikrein into $N^\alpha$-L-arginine and ethyl alcohol. The rate of splitting can be measured e.g. by spectrophotometric determination of the increasing extinction at the wave length 253 nm (nanometer). Among other ester substrates which are proteolytically split by kallikrein and which are useful for kallikrein determinations the following can be mentioned: $N^\alpha$-benzoyl-L-arginine methyl ester, $N^\alpha$-toluenesulfonyl-L-arginine methyl ester and $N^\alpha$-acetyl-L-tyrosine ethyl ester (cf. E.K. FREY et al., ibid., pages 12–14; and G. L. HABERLAND et al., "Kininogenases (Kallikrein)", 1st Symposium on Physiological Properties and Pharmacological Rational, F. K. Schattauer Verlag, Stuttgart-New York, 1973, p. 43 and 44). The enzymatic determination methods have the advantage of not requiring test animals, but have another serious disadvantage. The kallikrein solutions used for carrying out these methods must be optically clear and their concentration must be adjusted so that no substantial autoabsorption interferes at the wave length 253 nm. A further serious disadvantage of these enzymatic methods resides in the fact that the solution of the ester substrate (e.g. $N^\alpha$-benzoyl-L-arginine ethyl ester) used for the determination of kallikrein have a high auto-absorption (the extinction of a $5 \times 10^{-4}$ M solution in a cell of 1 cm at 253 nm is 2.1). At higher concentrations most UV spectrometers no longer show extinctions which are proportional to the concentrations used (cf. G. L. HABERLAND et al., ibid., p. 4).

A so-called amide substrate which is split amidolytically by certain enzymes of class E.C. 3.4.4. (in enzyme nomenclature the abbreviation "E.C." means "Enzyme Committee" of the "International Union of Biochemistry"), specifically thrombin and thrombin-like enzymes, is disclosed in German patent application DOS No. 2,322,116. This substrate comprises a base tripeptide chain of formula H-Phe-Val-Arg-OH which has its N-terminal amino acid blocked by a acyl group. The C-terminal amino acid carries as a substituent a chromogenic or fluorescent group which is split off by the proteolytic action of the said enzymes and yields a split product the quantity of which can be measured photometrically. This amide substrate is specifically adapted for the quantitative determination of thrombin and thrombin-like enzymes, but does not work at all in the determination of kallikrein, prekallikrein and similar enzymes.

The problem which had to be solved by the invention consisted in developing a new synthetic amide substrate which would be easily and rapidly split by kallikrein, more particularly plasma kallikrein, to yield split products which could easily be determined by spectrophotometric methods.

The solution of the said problem resulted from the following considerations: It was known that in humans suffering from or subjected to certain shocks or stresses the biologically highly active, pain-generating bradykinin is released from the naturally occurring substrate kininogen (molecular weight about 50,000) under the hydrolytic action of kallikrein. As a working hypothesis it was speculatively assumed that, by using a synthetic building unit corresponding to a C-terminal building unit of bradykinin and by attaching to the said synthetic building unit a chromogenic or fluorescent group, it might be possible to obtain a synthetic amide substrate which would have the same or almost the same susceptibility towards plasma kallikrein as the natural substrate and would yield by amidolysis a chromogenic or fluorescent split product having a high molecular extinction coefficient measurable at high wave lengths so as to minimize the influence of biological fluids on the measurement.

On the grounds of the above mentioned considerations a synthetic amide substrate meeting the defined requirements was developed.

SUMMARY OF THE INVENTION

Thus, the invention relates to a synthetic chromogenic or fluorescent amide substrate which is useful for the quantitative determination of certain proteolytic enzymes of class E.C. 3.4.4. in human and mammal body fluids as well as in vegetable and animal cell extracts and glandular venoms of cold-blooded animals such as snakes.

The substrate of this invention shows a high specificity in the quantitative determination of those enzymes which split peptide chains on the carboxyl side of arginine as well as lysine. More particularly, the said substrate is effective in the determination of enzymes such as plasma prekallikrein and indirectly its activators, plasma kallikrein and indirectly of its inhibitors and similar enzymes, enzymes in vegetable cell extracts, e.g. papain, and certain enzymes in snake venoms, e.g. prothrombin activators. However, the said substrate is inefficient in the determination of thrombin and thrombin-like enzymes.

The substrate of the invention essentially consists of a compound having the formula $$R^1 - Pro - X - Y - NH - R^2 \qquad I$$

wherein $R^1$ represents hydrogen, or an acyl or sulfonyl group, $R^2$ represents an aromatic hydrocarbon group which may carry substituents, X represents a phenylalanyl, β-cyclohexylalanyl, phenylglycyl or tyrosyl group and Y represents a protonized arginyl or lysyl group, and wherein $-NH-R^2$ is a chromogenic or fluorescent group. When subjected to the proteolytic action of the enzymes, this substrate splits and yields a split product of formula $NH_2-R^2$ the quantity of which can be measured by photometric, spectrophotometric or fluorescence-photometric methods.

DETAILED DESCRIPTION OF THE INVENTION

The acyl group $R^1$ in formula I can be further defined by the partial formula $R^3-CO-$ wherein $R^3$ represents
 a. an aliphatic hydrocarbon radical which comprises from 1 to 17 carbon atoms and which may carry an amino group in the ω-position;
 b. an araliphatic hydrocarbon radical which comprises from 1 to 17 carbon atoms and the aryl component of which may carry an amino group;
 c. a cycloaliphatic hydrocarbon radical which may carry an amino or aminomethyl group;
 d. an aromatic hydrocarbon radical which may carry an alkyl, amino or aminoalkyl group; or
 e. a benzyloxy group.

More particularly, $R^3$ can be an alkyl group such as methyl, ethyl, propyl, butyl, pentyl, etc., up to heptadecyl. These alkyl groups may carry an amino substituent in the ω-position. Thus, $R^3$ can be e.g. an ω-aminopropyl, ω-aminopentyl or ω-aminononyl group. Furthermore, $R^3$ can be a benzyl, 2-phenylethyl, 3-phenylpropyl, etc., up to 11-phenylundecyl group. The phenyl component of the said groups may carry an amino substituent in the para-position. Thus, $R^3$ can be a p-aminobenzyl, 2-(p-aminophenyl)-ethyl, 3-(p-aminophenyl)-propyl, etc., up to 11-(p-aminophenyl)-undecyl group. $R^3$ can also represent a cyclohexyl, 4-aminocyclohexyl, 4-aminomethylcyclohexyl, 4-aminoethylcyclohexyl, 4-aminopropylcyclohexyl or 4-aminobutylcyclohexyl group. Furthermore, $R^3$ can be a phenyl, α-naphthyl, β-naphthyl or biphenyl group. These groups may carry an amino, aminoalkyl or alkyl substituent. The alkyl can be e.g. methyl, ethyl, propyl, isopropyl, butyl or isobutyl.

The sulfonyl group represented by $R^1$ in formula I can be a benzene sulfonyl or p-toluene sulfonyl group.

$R^2$ can be e.g. a p-nitrophenyl, β-naphthyl or 4-methoxy-β-naphthyl group.

The invention further relates to the use of the above defined substrate in the quantitative determination of proteolytic enzymes of group E.C. 3.4.4. which split peptide chains on the carboxyl side of arginine as well as lysine, except thrombin and thrombin-like enzymes, in human and mammal body fluids as well as in vegetable or animal cell extracts and in glandular venoms of cold-blooded animals. More particularly, the said substrate is to be used for the quantitative determination of plasma prekallikrein and indirectly of its activators, of plasma kallikrein and indirectly of its inhibitors, of enzymes in vegetable cell extracts, e.g. papain, and prothrombin activators in snake venoms.

The substrate of the invention can be prepared by the following methods:

1. According to the first method the chromogenic groups ($R^2$ in formula I) are attached to the C-terminal amino acid group. These chromogenic groups at the same time protect the C-terminal carboxyl groups during the step-wide attachment of the amino acids in the process of building the desired peptide chain. The other protecting groups are selectively eliminated from the end product without the chromogenic group being affected. This method is described e.g. in "Peptide Synthesis" by Miklos BODANSZKY et al., Interscience Publishers, 1966, p. 163–165.

2. According to the second method the chromogenic group is attached to the finished peptide chain. When the stepwise synthesis of the required peptide chain is terminated, the C-terminal carboxy group is liberated by alkaline hydrolysis of the ester, and the chromogenic group is attached to the carboxy group. Finally, the remaining protective groups are selectively removed under conditions which do not affect the chromogenic group. This method is described e.g. in "Peptide Synthesis", ibid., p. 43 and 44.

3. According to a third method the chromogenic group is coupled to the finished peptide chain after removal of the protective groups. In this case the C-terminal carboxy group is liberated by a racemization-free enzymatic ester splitting. The esterolytic enzymes can be used as such or in combination with a matrix.

For protecting the $N^\alpha$-amino groups during the stepwise synthesis of the peptide chain common protective groups known to protect amino groups and to be split off selectively can be used. These protecting groups include in the first place Cbo, MeOCbo, $NO_2Cbo$, MCbo, BOC, TFA and formyl. The α-carboxy group of the amino acids can be activated by several known methods, e.g. by preparing the p-nitrophenyl ester, pentachlorophenyl ester, or N-hydroxysuccinimide ester derivatives and isolating these derivatives, or by preparing in situ the acid azides or anhydrides which may be either symmetrical or asymmetrical.

The activation of the carboxy group can also be achieved by means of a carbodiimide such as N,N'-dicyclohexylcarbodiimide.

The C-terminal carboxy group in the peptide derivatives is protected during the step-wise synthesis of the required peptide chain by means of the chromogenic amide group or by conversion into the methyl, ethyl, or isopropyl ester.

The other active free groups which do not participate in the synthesis of the peptide chain can be blocked by known methods. Thus, the δ-guanidino group of arginine may be protected by $NO_2$ or Tos or simply by protonization.

The preparation of the substrates of the invention is described in a more detailed manner in the following Examples.

The analysis of the eluates and products obtained according to the Examples was performed by thin layer-chromatography using glass plates coated with silica gel F254 (Merck). The thin layer-chromatograms were developed by means of the following solvent systems:
 A chloroform/methanol (9 : 1)
 B n-propanol/ethyl acetate/water (7 : 1 : 2)
 C n-butanol/acetic acid/water (3 : 1 : 1).

The chromatograms were developed first in UV light (254 nm) and then by the chlorine/toluidine reaction (cf. G. PATAKI: "Duennschichtchromatographie in der Aminosaeure- und Peptid-Chemie", Walter de Gruyter & Co., Berlin, 1966, p. 125).

The abbreviations used in the present specification and claims having the following means;

Arg = arginine
Ile = isoleucine
Leu = leucine
Lys = lysine
Pro = proline
Phe = phenylalanine
Tyr = tyrosine
Val = valine
C-Ph·Gly = C-phenylglycine
CHA = β-cyclohexylalanine Unless otherwise stated, all amino acids in the peptide chains have L-configuration.

AC = acetyl
$Ac_2O$ = acetic anhydride
AcOH = acetic acid
BOC = tert.- butyloxycarbonyl
Bz = benzoyl
Bzl = benzyl
$Bz_2O$ = benzoic anhydride
Cbo = carbonbenzoxy
DCCI = dicyclohexylcarbodiimide
DCHA = dicyclohexylamine
DCU = dicyclohexylurea
DMF = dimethylformamide
$Et_3N$ = triethylamine
HMPTA = N,N,N',N',N'',N''-hexamethylphosphoric acid triamide
MCbo = p-methoxyphenylazocarbobenzoxy
MeOH = methanol
NA = naphthylamine
OtBut = tert.-butyloxy
OEt = ethyloxy
OMe = methyloxy
OpNP = p-nitrophenoxy
pNA = p-nitroanilide
TFA = trifluoroacetyl
THF = tetrahydrofuran
Tos = p-toluenesulfonyl
TLC = thin layer chromatography

EXAMPLE 1

I. $N^\alpha$ -Bz-Pro-Phe-Arg-pNA·HCl a. $N^\alpha$ -Cbo-Arg($NO_2$)-pNA

1. In a 500 ml three-necked flask 32.55 g (92.1 mmoles) of well dried Cbo-Arg($NO_2$)-OH were dissolved in 200 ml of N,N,N',N',N'',N''-hexamethylphosphoric acid triamide which had been dried over $P_2O_5$ and freshly distilled, while keeping the atmosphere in the flask moisture-free. To the solution were added first 9.32 g (92.1 mmoles) of $Et_3N$ and then portionwise 18.90 g (115.1 mmoles) of p-nitrophenyl isocyanate (25% excess). The reaction mixture was kept at room temperature for 24 hours and then added dropwise, while stirring, to 1.5 liters of aqueous 2% $NaHCO_3$ solution. The precipitated product was isolated by filtration and washed three times with portions of 0.7 liter of aqueous 2% $NaHCO_3$ solution, three times with portions of 0.7 liter of distilled water, three times with portions of 0.5 liter of 0.5 N HCl and finally three times with potions of 0.5 liter of distilled water. The product was then dried in vacuo at 20° C and then extracted twice with portions of 200 ml of boiling MeOH. The major portion of $N^\alpha$ -Cbo-ω-nitroarginyl lactam formed as a by-product, but only a minute quantity of the desired product were thus dissolved. The obtained pre-purified product was dried and then extracted twice with portions of 50 ml of DMF heated to 70° C. The desired product was thus completely dissolved, whereas the by-product, N,N'-bis-p-nitrophenylurea remained undissolved. The DMF solution was concentrated in vacuo at 40° C. The addition of MeOH caused crystallization of a substance which was chromatographically homogeneous in solvent systems A and B and which melted at 186°–188.5° C. Yield: 29.75 g (68.2% of the theory).

The elementary analysis and the calculation from the empirical formula $C_{20}H_{23}N_7O_7$ gave the following values (the values for the empirical formula are put within brackets): C = 50.42% (50.74%); H = 4.98% (4.90%); N = 20.90% (20.71%). $[\alpha]_D^{22} = 1.27°$ ($c = 1.0$; AcOH).

2. In a 500 ml three-necked flask 17.7 g (50 mmoles) of dried Cbo—Arg($NO_2$)—OH were dissolved in 350 ml of THF/DMF (1 : 1), and then 5.05 g (50 mmoles) of $Et_3N$ were added to the solution, while the atmosphere in the flask was kept moisture-free. After cooling the reaction solution to −10° C, 6.85 g (50 mmoles) of isobutyl chloroformate dissolved in 30 ml of THF were added dropwise thereto within 15 minutes at a temperature kept between −10° and −5° C. After about 10 minutes a solution of 8.2 g (50 mmoles) of p-nitroaniline in 15 ml of DMF was added dropwise, again at a temperature kept between −10° and −5° C. After 2 hours the cooling was interrupted, and the reaction mixture was allowed to stand for 24 hours at room temperature. The solvents were removed by distillation in vacuo. The residue was washed three times with distilled water, three times with aqueous 5% $NaHCO_3$ solution and again with distilled water. After drying in vacuo the crude product was dissolved in MeOH, and the solution was passed through a column of "Sephadex LH-20" (cross-linked dextran gel) equilibrated with MeOH. A fraction of the eluate yielded 7.67 g (32.4% of the theory) of a product which had the same physical properties as the product prepared according to paragraph (1) of Example 1.

3. 17.7 g (50 mmoles) of Cbo-Arg($NO_2$)-OH were dissolved in 75 ml of DMF. After cooling to −10° C, 10.3 g (50 mmoles) of DCCI and 8.2 g (50 mmoles) of pNA were added to the solution. After 4 hours at −10° C and 20 hours at 20° C the precipitated DCU was removed by filtration, and the filtrate was concentrated in dryness. After dissolution of the crude product in MeOH the solution was passed through a column of "Sephadex LH-20" equilibrated with MeOH. From a fraction of the eluate a major proportion of by-product, i.e. N—Cbo—Arg($NO_2$)—N,N'-dicyclohexylurea, and 4.32 g (17.9% of the theory) of the desired product were obtained. This product had the same physical properties as the product prepared according to paragraph (1) of Example 1.

b. $N^\alpha$ -Cbo-Phe-Arg($NO_2$)-pNA 9.5 g (20 mmoles) of $N^\alpha$ -Cbo-Arg($NO_2$)-pNA (prepared according to Example 1, paragraph (a)), were dissolved, while stirring, in 80 ml of 2N HBr in glacial acetic acid within 1 hour at 20° C in the absence of moisture. The dissolution was accompanied by $CO_2$ generation. The reaction solution was added slowly, with vigorous stirring, to 400 ml of anhydrous ether. This resulted in the precipitation of HBr.H — Arg(NO$_2$) —pNA. The ethereal phase was sucked off through a filter rod. The remaining precipitate was washed four times with portions of 150 ml of dry ether in order to remove benzyl bromide which had formed as well as excess HBr and AcOH. After drying over NaOH platelets the deblocked product was obtained in a quantitative yield. The dry hydrobromide derivative was dissolved in 50 ml of DMF. After cooling of the solution to −10° C, 4.16 ml (30 mmoles) of Et$_3$N were added thereto in order to release H-Arg(NO$_2$)pNA from the hydrobromide. The Et$_3$N.HBr salt which had formed was sucked off and washed with a small quantity of cold DMF. 7.8 g (21 mmoles) of Cbo-Phe-OpNP were added to the filtrate at −10° C. After a few hours the reaction solution had reached room temperature. The solution was again cooled to −10° C and then buffered with 1.4 ml (10 mmoles) of Et$_3$N. After about 5 hours a further 1.4 ml of Et$_3$N was added. After further 24 hours the reaction solution was concentrated to dryness in vacuo at 40° C. The residue was digested three times with portions of 100 ml of distilled water and then again dried in vacuo over NaOH platelets at 40° C. The dried product was recrystallized from MeOH to obtain 7.84 g of a product which was chromatographically homogeneous in solvent systems A and B. After gel filtration of the mother liquor through a column of "Sephadex LH-20" equilibrated with MeOH a further crop of 3.14 g of the same product was obtained. Thus, a total of 10.98 g (88.5 % of the theory) of homogeneous product melting at 203°–205° C was obtained.

The elementary analysis and the calculation from the empirical formula $C_{29}H_{32}N_8O_8$ yielded the following values (the values from the empirical formula are put within brackets): C = 55.88 % (C = 56.12%); H = 5.05 % (H = 5.20 %); N = 18.31 % (N = 18.06 %).

c. N$^\alpha$ -Cbo-Pro-Phe-Arg(NO$_2$)-pNa 31.0 g (50 mmoles) of N$^\alpha$ -Cbo-Phe-Arg(NO$_2$)-pNA (prepared according to Example 1, paragraph (b)) were treated with 250 ml of 2 N HBr in glacial acetic acid (0.5 mole). The reaction product was treated in the manner described in Example 1, paragraph (b). After drying in vacuo over NaOH platelets the dry hydrobromide of the dipeptide derivative was dissolved in 150 ml of DMF. After cooling 7.5 g of Et$_3$N dissolved in 15 ml of DMF (75 mmoles) were added to the solution. The Et$_3$N.HBr which had formed was removed by filtration and washed with a small quantity of cold DMF. To the filtrate 18.5 g (50 mmoles) of Cbo-pro-OpNP were added. The reaction product was treated in the manner described in paragraph (b) of Example 1. By gel filtration through a column of "Sephadex LH-20" equilibrated with MeOH and elution, 30.9 g (86.2 % of the theory) of a product which was chromatographically homogeneous in solvent systems A and B and which melted at 184°–186° C were obtained. The elementary analysis and the calculation from the empirical formula $C_{34}H_{39}N_9O_9$ gave the following values (the values from the empirical formula are put within brackets): C = 56.75 % (56.90%); H = 5.50 % (5.48%); N = 17.70 % (17.56%).

d. N$^\alpha$ -Bz-Pro-Phe-Arg(NO$_2$)-pNA 14.4 g (20 mmoles) of N$^\alpha$ -Cbo-Pro-Phe-Arg(NO$_2$)-pNA (prepared according to paragraph (c) of Example 1) were treated with 120 ml of 2 N HBr in glacial acetic acid (0.24 mole). The reaction mixture was further treated in the manner described in paragraph (b) of Example 1.

The dried tripeptide-hydrobromide derivative was dissolved in 60 ml of DMF. After cooling 4.16 ml (30 mmoles) of Et$_3$N were added to the solution. The Et$_3$N.HBr which had formed was removed by filtration and washed with a small quantity of cold DMF. To filtrate 6.8 g (30 mmoles) of benzoic acid anhydride were added. The reaction solution was buffered and then further treated in the manner described in paragraph (b) of Example 1. The crude product was purified on a column of "Sephadex LH-20" equilibrated with MeOH. There were thus obtained 11.3 g (82 % of the theory) of an amorphous product which was chromatographically homogeneous in solvent systems A and B.

The elementary analysis and the calculation from the empirical formula $C_{33}H_{37}N_9O_8$ gave the following values: C = 57.51% (57.63%); H = 5.38 % (5.42%); N = 18.47 % (18.33%).

e. N$^\alpha$ -Bz-Pro-Phe-Arg-pNA.HCl 688 mg (1 mmole) of N$^\alpha$ -Bz-Pro-Phe-Arg(NO$_2$)-pNA (prepared according to paragraph (d) of Example 1) were weighed in in the reaction vessel of a Sakabibara apparatus. Then 10 ml of dry hydrofluoric acid gas were condensed in the reaction vessel. The reaction was allowed to proceed for 1 hour at 0° C, while stirring, and resulted in the removal of the protective nitro group. The condensed hydrofluoric acid was removed by distillation in vacuo, and the residue was dissolved in DMF. In order to convert the peptide derivative into its hydrochloride 0.5 ml of concentrated HCl was added to the solution. The solution was concentrated to dryness. After having repeated twice these operations the residue was dissolved in 50 ml of 30% aqueous AcOH. The AcOH solution was purified on a column of "Sephadex G-15" equilibrated with 30% aqueous AcOH and eluated with 30% aqueous AcOH. Freeze-drying of part of the eluate yielded 572 mg (84.2 % of the theory) of an amorphous powder which was chromatographically homogeneous in solvent system C.

The elementary analysis and the calculation from the empirical formula $C_{33}H_{39}N_8O_6Cl$ gave the following values: C = 58.12 % (58.36%); H = 5.70 % (5.79%; N = 16.65 % (16.50%) and Cl = 5.15 % (5.22 %).

The amino acid analysis confirmed the expected presence of amino acids in the correct proportions: Arg: 0.98 — Phe: 1.0 — Pro: 0.97.

EXAMPLES 2

II. H-Pro-Phe-Arg-pNA.2HCl 718 mg (1 mmole) of N$^\alpha$ -Cbo-Pro-Phe-Arg(NO$_2$)-pNA (prepared according to paragraph (c) of Example 1) were weighed in in the reaction vessel of a Sakakibara apparatus. 10 ml of dry hydrofluoric acid gas were condensed in the reaction vessel. The reaction was allowed to proceed for 1 hour at 0° C, while stirring, and resulted in the removal of the protective nitro group. The condensed hydrofluoric acid was removed by distillation in vacuo, and the residue was dissolved in DMF. In order to convert the peptide derivative into its hydrochloride salt, 0.5 ml of concentrated HCl was added to the solution, and the solution was concentrated to dryness. After having repeated twice these operations the residue was dissolved in 50 ml of 30% aqueous AcOH. The solution was purified on a column of "Sephadex G-15" equilibrated with 30% aqueous AcOH and eluted with 30% aqueous AcOH. Freeze-drying of part of the eluate yielded 385 mg (63.0% of the theory) of an amorphous powder which was chromatographically homogeneous in solvent system C.

The elementary analysis and the calculation from the empirical formula $C_{26}H_{36}N_8O_5Cl_2$ gave the following values: C = 50.95% (51.06%); H = 5.90% (5.93%); N = 18.41 % (18.32%); and Cl = 11.52 % (11.60%).

The amino acid analysis confirmed the presence of the expected amino acids in the correct proportions: Arg: 0.95 — Phe: 1.00 — Pro: 1.00.

EXAMPLE 3

III. $N^\alpha$-Ac-Pro-Phe-Arg-pNA.HCl

IIIa. $N^\alpha$-Ac-Pro-Phe-Arg($NO_2$)-pNA 1.44 g (2 mmoles) of the compound prepared according to Example 1, paragraph I (c), were deblocked by the method described in Example 1, paragraph (b) and then dissolved in 10 ml of DMF. 420 μl (3 mmoles) of $Et_3N$ were added to the solution. After cooling 400 μm (~ 4 mmoles) of $Ac_2O$ were added to the reaction mixture which was then further treated according to Example 1, paragraph I (d). Purification: gel filtration on "Sephadex LH-20" in MeOH. Yield: 1.05 g of amorphous substance (83.9 % of the theory) which was homogeneous according to TLC in the solvent system (SS) A and B. Elementary analysis and calculation from the empirical formula $C_{28}H_{35}N_9O_8$ gave the following values: C = 53.68% (53.75%); H = 5.60% (5.64%); N = 20.20% (20.15%).

III. $N^\alpha$-Ac-Pro-Phe-Arg-pNA.HCl 626 mg (1 mmole) of compound IIIa were reacted according to Example 1, paragraph I (e) in order to form compound III. Purification: gel filtration on "Sephadex G-15" in 30% AcOH. Yield: 521 mg of freeze-dried amorphous powder (84.4% of the theory) which was homogeneous according to TLC in SS C. Elementary analysis and calculation from the empirical formula $C_{26}H_{37}N_8O_6Cl$ gave the following values: C = 54.25% (54.50%); H = 6.01% (6.04%); N = 18.25% (18.16%); Cl = 5.71% (5.75%). The amino acid analysis confirmed the presence of the expected amino acids in the correct proportions: Arg: 0.99 — Phe 1.00 — Pro: 0.97.

EXAMPLE 4

IV. $N^\alpha$-Caproyl-Pro-Phe-Arg-pNA.HCl

IVa. $N^\alpha$-Caproyl-Pro-Phe-Arg($NO_2$)-pNA 718 mg (1 mmole) of the compound prepared according to Example 1, paragraph I (c), were deblocked by the method described in Example 1, paragraph I (b), and then dissolved in 10 ml of DMF. 210 μl (1.5 mmoles) of $Et_3N$ were added to the solution. After cooling 400 mg (~ 1.5 mmoles) of p-nitrophenyl caproate were added to the reaction mixture which was then further treated according to Example 1, paragraph I (b). Purification: gel filtration on "Sephadex LH-20" in MeOH. Yield: 490 mg of amorphous substance (68.8% of the theory) which was homogeneous according to TLC in the SS A and B. Elementary analysis and calculation from the empirical formula $C_{34}H_{49}N_9O_8$ gave the following values: C = 57.51% (57.37%); H = 6.88% (6.94%); N = 17.80% (17.71%).

IV. $N^\alpha$-Caproyl-Pro-Phe-Arg-pNA.HCl 356 mg (0.5 mmole) of compound IVa were reacted according to Example 1, paragraph I(e) in order to form compound IV. Purification: gel filtration on "Sephadex G-15" in 30% AcOH. Yield: 226 mg of freeze-dried amorphous powder (64.3% of the theory) which was homogeneous according to TLC in SS C. Elementary analysis and calculation from the empirical formula $C_{34}H_{51}N_8O_6Cl$ gave the following values: C = 57.92% (58.07%); H = 7.18% (7.31%); N = 16.08% (15.93%); Cl = 4.98% (5.04%).

The amino acid analysis confirmed the presence of the expected amino acids in the correct proportions: Arg: 0.99 — Phe: 1.00 — Pro: 0.95.

EXAMPLE 5

V. $N^\alpha$-cyclohexylcarbonyl-Pro-Phe-Arg-pNA.HCl

Va. $N^\alpha$-Cyclohexylcarbonyl-Pro-Phe-Arg($NO_2$)-pNA 718 mg (1 mmole) of the compound prepared according to Example 1, paragraph I (c), were deblocked by the method described in Example 1, paragraph I (b), and then dissolved in 10 ml of DMF. 210 μl (1.5 mmoles) of $Et_3N$ were added to the solution. After cooling 375 mg (1.5 mmoles) of p-nitro-phenyl cyclohexanecarboxylate were added to the reaction mixture which was then further treated according to Example 1, paragraph I (b). Purification: gel filtration on "Sephadex LH-20" in MeOH. Yield: 593 mg of amorphous substance (85.5% of the theory) which was homogeneous according to TLC in the SS A and B. Elementary analysis and calculation from the empirical formula $C_{33}H_{43}N_9O_8$ gave the following values: C = 57.01% (57.13%); H = 6.18% (6.25%); N = 18.30% (18.17%).

V. $N^\alpha$-Ac-Pro-Phe-Arg-pNA.HCl 347 mg (0.5 mmole) of compound Va were reacted according to Example 1, paragraph I (e) in order to form compound V. Purification: gel filtration on "Sephadex G-15" in 30% AcOH. Yield: 295 mg of freeze-dried amorphous powder (86.1% of the theory) which was homogeneous according to TLC in SS C. Elementary analysis and calculation from the empirical formula $C_{33}H_{45}N_8O_6Cl$ gave the following values: C = 57.70% (57.84%); H = 6.66% (6.62%); N = 16.40% (16.35%); Cl = 5.11% (5.17%).

The amino acid analysis confirmed the presence of the expected amino acids in the correct proportions: Arg: 0.97 — Phe: 1.00 — Pro: 0.95.

EXAMPLE 6

VI. $N^\alpha$-4-Methyl-Bz-Pro-Phe-Arg-pNA.HCl

VIa. $N^\alpha$-4-Methyl-Bz-Pro-Phe-Arg($NO_2$)-pNA 718 mg (1 mmole) of the compound prepared according to Example 1, paragraph I (d), were deblocked by the method described in Example 1, paragraph (b), and then dissolved in 10 ml of DMF. 210 μl (1.5 mmoles) of $Et_3N$ were added to the solution. After cooling 386 mg (1.5 mmoles) of p-nitrophenyl p-toluenesulfonate were added to the reaction mixture which was then further treated according to Example 1, paragraph I (b). Purification: gel filtration on "Sephadex LH-20" in MeOH. Yield: 591 mg of amorphous substance (84.2% of the theory) which was homogeneous according to TLC in the SS A and B. Elementary analysis and calculation from the empirical formula $C_{34}H_{39}N_9O_8$ gave the following values: C = 58.07% (58.19%); H = 5.53% (5.60%); N = 18.06% (17.97).

VI. $N^\alpha$ -4-Methyl-Bz-Pro-Phe-Arg-pNA.HCl 351 mg (0.5 mmole) of compound VIa were reacted according to Example 1, paragraph I (e) in order to form compound VI. Purification: gel filtration on "Sephadex G-15" in 30% AcOH. Yield: 248 mg of freeze-dried amorphous powder (71.5% of the theory) which was homogeneous according to TLC in SS C. Elementary analysis and calculation from the empirical formula $C_{34}H_{41}N_8O_6Cl$ gave the following values: C = 59.01% (58.91%); H = 5.86% (5.96%); N = 16.31% (16.17%); Cl = 5.07% (5.11%).

The amino acid analysis confirmed the presence of the expected amino acids in the correct proportions: Arg: 0.96 — Phe: 1.00 — Pro: 0.96.

EXAMPLE 7

VII. $N^\alpha$ -3-Phenyl-propionyl-Pro-Phe-Arg-pNA.HCl

VIIa.

$N^\alpha$ -3-Phenyl-propionyl-Pro-Phe-Arg($NO_2$)-pNA 718 mg (1 mmole) of the compound prepared according to Example 1, paragraph I (c), were deblocked by the method described in Example 1, paragraph I (b), and then dissolved in 10 ml of DMF. 210 μl (1.5 mmoles) of $Et_3N$ were added to the solution. After cooling 407 μl (1.5 mmoles) of p-nitrophenyl dihydrocinnamate were added to the reaction mixture which was then further treated according to Example 1, paragraph I (b). Purificaton: gel filtration on "Sephadex LH-20" in MeOH. Yield: 547 mg of amorphous substance (76.4% of the theory) which was homogeneous according to TLC in the SS A and B. Elementary analysis and calculation from the empirical formula $C_{35}H_{41}N_9O_8$ gave the following values: C = 58.58% (58.73%); H = 5.69% (5.77%); N = 18.82% (17.61%).

VII. $N^\alpha$ -3-Phenyl-propionyl-Pro-Phe-Arg-pNA.HCl 358 mg (0.5 mmole) of compound VIIa were reacted according to Example 1, paragraph I (e) in order to form compound VII. Purification: gel filtration on "Sephadex G-15" in 30% AcOH. Yield: 303 mg of freeze-dried amorphous powder (85.7% of the theory) which was homogeneous according to TLC in SS C. Elementary analysis and calculation from the empirical formula $C_{35}H_{43}N_8O_6Cl$ gave the following values: C = 59.24% (59.44%); H = 6.11% (6.13%); N = 15.98% (15.85%); Cl = 4.93% (5.01%).

The amino acid analysis confirmed the presence of the expected amino acids in the correct proportions: Arg: 0.98 — Phe: 1.00 — Pro: 1.01.

EXAMPLE 8

VIII. $N^\alpha$ -(ω-Aminocaproyl)-Pro-Phe-Arg-pNA.2HCl

VIIIa.

$N^\alpha$ -($N^\omega$ -Cbo-Aminocaproyl)-Pro-Phe-Arg($NO_2$)-pNA 718 mg (1 mmole) of the compound prepared according to Example 1, paragraph I (c), were deblocked by the method described in Example 1, paragraph I (b), and then dissolved in 10 ml of DMF. 210 μl (1.5 mmoles) of $Et_3N$ were added to the solution. After cooling 490 mg (1.25 mmoles) of p-nitrophenyl $N^\omega$ -Cbo-ω-aminocaproate were added to the reaction mixture which was then further treated according to Example 1, paragraph I (b). Purification: gel filtration on "Sephadex LH-20" in MeOH. Yield: 698 mg of amorphous substance (84.0% of the theory) which was homogeneous according to TLC in the SS A and B. Elementary analysis and calculation from the empirical formula $C_{40}H_{50}N_{10}O_{10}$ gave the following values: C = 57.68% (57.82%); H = 6.01% (6.07%); N = 17.02% (16.86%).

VIII. $N^\alpha$ -(ω-Aminocaproyl)-Pro-Phe-Arg-pNA.2HCl 415 mg (0.5 mmole) of compound VIIIa were reacted according to Example 1, paragraph I (e) in order to form compound VIII. Purification: gel filtration on "Sephadex G-15" in 30% AcOH. Yield: 247 mg of freeze-dried amorphous powder (69.2% of the theory) which was homogeneous according to TLC in SS C. Elementary analysis and calculation from the empirical formula $C_{32}H_{47}N_9O_6Cl_2$ gave the following values: C = 52.85% (53.04%); H = 6.50% (6.54%); N = 17.53% (17.40%); Cl = 9.69% (9.79%).

The amino acid analysis confirmed the presence of the expected amino acids in the correct proportions: Arg: 0.98 — Phe: 1.00 — Pro: 0.95.

EXAMPLE 9

IX.

$N^\alpha$ -4-Aminomethyl-cyclohexylcarbonyl-Pro-Phe-Arg-pNA.2HCl

IXa.

$N^\alpha$ -4-Cbo-Aminomethyl-cyclohexylcarbonyl-Pro-Phe-Arg($NO_2$)-pNA 7.18 mg (1 mmole) of the compound prepared according to Example 1, paragraph I (c), were deblocked by the method described in Example 1, paragraph I (b), and then dissolved in 10 ml of DMF. 210 μl (1.5 mmoles) of $Et_3N$ were added to the solution. After cooling 455 mg (1.1 mmoles) of p-nitrophenyl 4-Cbo-aminomethyl-cyclohexanecarboxylate were added to the reaction mixture which was then further treated according to Example 1, paragraph I (b). Purification: gel filtration on "Sephadex LH-20" in MeOH. Yield: 762 mg of amorphous substance (88.9% of the theory) which was homogeneous according to TLC in the SS A and B. Elementary analysis and calculation from the empirical formula $C_{42}H_{52}N_{10}O_{10}$ gave the following values: C = 58.62% (58.87%); H = 6.05% (6.12%); N = 16.54% (16.35%).

IX.

$N^\alpha$ -4-Aminomethyl-cyclohexylcarbonyl-Pro-phe-Arg-pNA.2HCl 428 mg (0.5 mmole) of compound IXa were reacted according to Example 1, paragraph I (e) in order to form compound IX. Purification: gel filtration on "Sephadex G-15" in 30% AcOH. Yield: 198 mg of freeze-dried amorphous powder (52.7% of the theory) which was homogeneous according to TLC in SS C. Elementary analysis and calculation from the empirical formula $C_{34}H_{49}N_9O_6Cl$ gave the following values: C = 54.22% (54.40%); H = 6.53% (6.58%); N = 16.74% (16.58%); $C_1$ = 9.35% (9.45%).

The amino acid analysis confirmed the presence of the expected amino acids in the correct proportions: Arg: 0.99 — Phe: 1.00 — Pro:1.01.

EXAMPLE 10

X. $N^\alpha$ -Tos-Pro-Phe-Arg-pNA.HCl HCl

Xa. $N^\alpha$ -Tos-Pro-Phe-Arg($NO_2$)-pNA 718 mg (1 mmole) of the compound prepared according to Example 1, paragraph I (c), were deblocked by the method described in Example 1, paragraph I (b), and then dissolved in 10 ml of DMF. 210 μl (1.5 mmoles) of $Et_3N$ were added to the solution. After cooling 380 mg (2 mmoles) of tosyl chloride were added to the reaction mixture which was then further treated according to Example 1, paragraph I (d). Purification: gel filtration on "Sephadex LH-20" in MeOH. Yield: 225 mg of amorphous substance (30.5% of the theory) which was homogeneous according to TLC in the SS A and B. Elementary analysis and calculation from the empirical formula $C_{33}H_{39}N_9O_9S$ gave the following values: C = 53.59% (53.72%); H = 5.31% (5.33%); N = 17.29% (17.09%); S = 4.15% (4.35%).

X. $N^\alpha$ -Tos-Pro-Phe-Arg-pNA.HCl HCl 185 mg (0.25 mmole) of compound Xa were reacted according to Example 1, paragraph I (e) in order to form compound X. Purification: gel filtration on "Sephadex G-15" in 30% AcOH. Yield: 127 mg of freeze-dried amorphous powder (69.6% of the theory) which was homogeneous according to TLC in SS C. Elementary analysis and calculation from the empirical formula $C_{33}H_{41}N_8O_7ClS$ gave the following values: C = 54.18% (54.35%); H = 5.63% (5.67%); N = 15.52% (15.37%); Cl = 4.80% (4.86%); S = 4.44% (4.40%).

The amino acid analysis confirmed the presence of the expected amino acids in the correct proportions: Arg: 0.95 — Phe: 1.00 — Pro: 0.97.

EXAMPLE 11

XI.

$N^\alpha$ -4-Aminophenyl-acetyl-Pro-Phe-Arg-pNA.2HCl

XIa.

$N^\alpha$ -4-Cbo-Aminophenyl-acetyl-Pro-Phe-Arg($NO_2$)-pNA 718 mg (1 mmole) of the compound prepared according to Example 1, paragraph I(c), were deblocked by the method described in Example 1, paragraph I(b), and then dissolved in 10 ml of DMF. 210 μl (1.5 mmoles) of $Et_3N$ were added to the solution. After cooling 508 mg d(1.25 mmoles) of p-nitrophenyl 4-Cbo-aminophenyl-acetate were added to the reaction mixture which was then further treated according to Example 1, paragraph I (b). Purification: gel filtration on "Sephadex LH-20" in MeOH. Yield: 595 mg of amorphous substance (69.9% of the theory) which was homogeneous according to TLC in the SS A and B. Elementary analysis and calculation from the empirical formula $C_{42}H_{46}N_{10}O_{10}$ gave the following values: C = 58.96% (59.29%); H = 5.38% (5.45%); N = 16.55% (16.46%).

XI.

$N^\alpha$ -4-Aminophenyl-acetyl-Pro-Phe-Arg-pNA.2HCl 425 mg (0.5 mmole) of compound XIa were reacted according to Example 1, paragraph I (e) in order to form compound XI. Purification: gel filtration on "Sephadex G-15" in 30% AcOH. Yield: 315 mg of freeze-dried amorphous powder (84.6% of the theory) which was homogeneous according to TLC is SS C. Elementary analysis and calculation from the empirical formula $C_{34}H_{43}N_9O_6Cl_2$ gave the following values: C = 54.72% (54.84%); H = 5.80% (5.82%); N = 17.08% (16.93%); Cl = 9.43% (9.52%).

The amino acid analysis confirmed the presence of the expected amino acids in the correct proportions: Arg: 0.99 — Phe: 1.00 — Pro: 0.96.

EXAMPLE 12

XII. $N^\alpha$ -4-Aminobenzoyl-Pro-Phe-Arg-pNA.2HCl

XIIa.

$N^\alpha$ -4-Cbo-Aminobenzoyl-Pro-Phe-Arg($NO_2$)-pNA 718 mg (1 mmole) of the compound prepared according to Example 1, paragraph I (c), were deblocked by the method described in Example 1, paragraph I (b), and then dissolved in 10 ml of DMF. 210 μl (1.5 mmoles) of $Et_3N$ were added to the solution. After cooling 490 mg (1.25 mmoles) of p-nitrophenyl 4-Cbo-aminobenzoate were added to the reaction mixture which was then further treated according to Example 1, paragraph I (b). Purification: gel filtration on "Sephadex LH-20" in MeOH. Yield: 693 mg of amorphous substance (82.8% of the theory) which was homogeneous according to TLC in the SS A and B. Elementary analysis and calculation from the empirical formula $C_{41}H_{44}N_{10}O_{10}$ gave the following values: C = 58.92% (58.84%); H = 5.16% (5.30%); N = 16.93% (16.74%).

XII. $N^\alpha$ -4-Aminobenzoyl-Pro-Phe-Arg-pNA.2HCl 418 mg (0.5 mmole) of compound XIIa were reacted according to Example 1, paragraph I (e) in order to form compound XII. Purification: gel filtration on "Sephadex G-15" in 30% AcOH. Yield: 282 mg of freeze-dried amorphous powder (77.2% of the theory) which was homogeneous according to TLC in SS C. Elementary analysis and calculation from the empirical formula $C_{33}H_{41}N_9O_6Cl_2$ gave the following values: C = 54.09% (54.25%); H = 5.60% (5.66%); N = 17.48% (17.25%); Cl = 9.65% (9.71%).

The amino acid analysis confirmed the presence of the expected amino acids in the correct proportions: Arg: 0.95 — Phe: 1.00 — Pro: 0.97.

EXAMPLE 13

XIII. $N^\alpha$ -Cbo-Pro-Phe-Arg-pNA.HCl

XIIIa. Cbo-Arg-pNA.HCl

In a 250 ml three-necked flask 16.0 g (47 mmoles) of Cbo-Arg-OH.HCl, dried over $P_2O_5$ in vacuo, were dissolved in 90 ml of absolute HMPTA in a moisture-free atmosphere at 20° C. To the resulting solution there was first added portionwise a solution of 4.74 g (47 mmoles) of $Et_3N$ in 10 ml of HMPTA and then 16.4 g (100 mmoles) of p-nitrophenyl isocyanate (100% excess) at room temperature. The reaction mixture was kept at room temperature for 24 hours, whereupon most of the HMPTA was distilled off in vacuo. The residue was extracted several times with 30% AcOH. The residue was discarded. The combined AcOH extracts were further purified by gel filtration on a "Sephadex G-15" column as described in Example 1, paragraph I (e). After freeze-drying of part of the eluate 12.6 g of an amporphous powder were obtained which was homogeneous according to TLC in the SS C and which was split by trypsin with liberation of pNA. Elementary analysis and calculation from the empirical formula $C_{20}H_{25}N_6O_5Cl$ gave the following values: C = 51.29% (51.67%); H = 5.48% (5.42%); N = 17.92% (18.08%); Cl = 7.50% (7.63%).

XIIIb. $N^\alpha$-Cbo-Phe-Arg-pNA.HCl 7.0 g (15 mmoles) of compound XIIIa were deblocked in a moisture-free atmosphere and further treated according to Example 1, paragraph I (b). The resulting product was dissolved in 75 ml of DMF and after cooling a solution of 1.52 g of $Et_3N$ in 10 ml of DMF was added thereto, whereupon the $Et_3N$.HBr which had formed was filtered off. 8.4 g (20 mmoles) of Cbo-Phe-OpNP were added to the filtrate. The reaction was further carried out as described in Example 1, paragraph I (b). The reaction solution was concentrated to dryness in vacuo at 40° C and the residue was dissolved in 250 ml of MeOH. To the solution 1.20 ml of conc. HCl was added. The crude product was purified by gel filtration on a column of "Sephadex LH-20" in MeOH. Concentration in vacuo of a fraction gave 7.55 g (82.2% of the theory) of the desired product which was homogeneous according to TLC in the SS C. Elementary analysis and calculation from the empirical formula $C_{29}H_{34}N_7O_6Cl$ gave the following values: C = 57.09% (56.91%); H = 5.50% (5.60%); N = 16.25% (16.02%); Cl = 5.71% (5.79%).

XIII. $N^\alpha$-Cbo-Pro-Phe-Arg-pNA.HCl 673 mg (1.1 mmole) of compound XIIIb were deblocked in a moisture-free atmosphere and further treated according to Example 1, paragraph I (b). The dried hydrobromide derivative was dissolved in 10 ml of DMF and after cooling (−10° C) 155 µl (1.1 mmole) of $Et_3N$ were added to the solution. 555 mg (1.5 mmole) of Cbo-Pro-OpNP were then added. After 24 hours' reaction the reaction solution was concentrated to dryness in vacuo. The residue was dissolved in 30 ml of MeOH and filtered through a column of "Sephadex LH-20" equilibrated with MeOH. The eluate was further purified by concentration in vacuo, and the residue was dissolved in 30% AcOH. The solution was filtered through a column of "Sephadex G-15". After freeze-drying of part of the eluate and addition of 90 µl conc. HCl 479 mg (61.4% of the theory) of an amorphous powder were obtained which was homogeneous according to TLC in the SS C. Elementary analysis and calculation from the empirical formula $C_{34}H_{41}N_8O_7Cl$ gave the following values: C = 57.11% (57.58%); H = 5.71% (5.83%); N = 16.15% (15.80%); Cl = 4.92% (5.00%).

The amino acid analysis confirmed the presence of the expected amino acids in the correct proportions: Arg: 0.95 — Phe: 1.00 — Pro: 0.98.

EXAMPLE 14

XIV. $N^\alpha$-Bz-Pro-CHA-Arg-pNA.HCl

XIVa. $N^\alpha$-Cbo-CHA-Arg($NO_2$)-pNA 9.47 g (20 mmoles) of the compound prepared according to Example 1, paragraph I (a) were deblocked by the method described in Example 1, paragraph I (b). The dried residue was dissolved in 100 ml of DMF. After cooling 3.04 g (30 mmoles) of $Et_3N$ were added to the solution. The HBr.$Et_3N$ which had formed was filtered off. 9.37 g (22 mmoles) of Cbo-CHA-OpNP were added at −10° C to the filtrate. The reaction mixture was further treated according to Example 1, paragraph I (b). After gel filtration on "Sephadex LH-20" in MeOH 11.72 g (93.5% of the theory) of crystalline compound XIVa were obtained. This compound melted at 166°–168° C and was homogeneous according to TLC in the SS A and B. Elementary analysis and calculation from the empirical formula $C_{29}H_{38}N_8O_8$ gave the following values: C = 55.20% (55.58%); H = 5.98% (6.11%); N = 18.01% (17.88%).

XIVb. $N^\alpha$-Cbo-Pro-CHA-Arg($NO_2$)-pNA 6.27 g (10 mmoles) of compound XIVa were deblocked according to Example 1, paragraph I (b). The dry hydrobromide derivative was dissolved in 75 ml of DMF. After cooling 2.08 ml (15 mmoles) of $Et_3N$ were added to the solution. The HBr.$Et_3N$ which had formed was filtered off. 4.07 g (11 mmoles) of Cbo-Pro-OpNP were added at −10° C to the filtrate. The reaction mixture was further treated according to Example 1, paragraph I (b). After gel filtration on "Sephadex LH-20" in MeOH 6.18 g (85.4% of the theory) of the amorphous compound XIVb were obtained. This compound was homogeneous according to TLC in the SS A and B. Elementary analysis and calculation from the empirical formula $C_{34}H_{45}N_9O_9$ gave the following values: C = 56.22% (56.42%); H = 6.14% (6.27%); N = 17.35% (17.42%).

XIVc. $N^\alpha$-Bz-Pro-CHA-Arg($NO_2$)pNA 1.45 g (2 mmoles) of compound XIVb were deblocked by the method described in Example 1, paragraph I (b). The resulting dry hydrobromide derivative was dissolved in 15 ml of DMF. After cooling (−10° C) 0.30 g (3 mmoles) of $Et_3N$ and then 680 mg (3 mmoles) of $Bz_2O$ were added to the solution. The reaction mixture was then further treated according to Example 1, paragraph I (d). The resulting crude product was dissolved in MeOH and purified by filtration on a column of "Sephadex LH-20" in MeOH. Yield: 1.03 g of amorphous substance XIVc (74.2% of the theory) which was homogeneous according to TLC in the SS A and B. Elementary analysis and calculation from the empirical formula $C_{33}H_{43}N_9O_8$ gave the following values: C = 57.29% (57.13%); H = 6.30% (6.25%); N = 18.09% (18.17%).

XIV. $N^\alpha$-Bz-Pro-CHA-Arg-pNA.HCl 694 mg (1 mmole) of compound XIVc were reacted according to Example 1, paragraph I (e), in order to form compound XIV. Purification: gel filtration on "Sephadex G-15" in 30% AcOH. Yield: 571 mg of freeze-dried amorphous powder (83.3% of the theory) which was homogeneous according to TLC in SS C. Elementary analysis and calculation from the empirical formula $C_{33}H_{45}N_8O_6Cl$ gave the following values: C = 57.15% (57.84%); H = 6.49% (6.62%); N = 16.70% (16.35%): Cl = 5.09% (5.17%).

The amino acid analysis confirmed the presence of the expected amino acids in the correct proportions: Arg: 1.04 — CHA: 1.02 — Pro: 1.00.

EXAMPLE 15

XV. $N^\alpha$-Bz-Pro-Tyr-Arg-pNA.HCl

XVa. $N^\alpha$-Cbo-Tyr(OBzl)-Arg($NO_2$)-pNA 2.37 g (5 mmoles) of compound I (a) (cf. Example 1) were deblocked by the method described in Example 1, paragraph I (b). The resulting dry hydrobromide derivative was dissolved in 30 ml of DMF. After cooling 1.05 ml (7.5 mmoles) of Et₃N and then 2.82 g (5.5 mmoles) of Cbo-Tyr(OBzl)-OpNP were added to the solution. The reaction mixture was then further treated according to Example 1, paragraph I (b). After gel filtration on "Sephadex LH-20" in MeOH 1.78 g (49.0% of the theory) of the amorphous compound XVa were obtained. This compound was homogeneous according to TLC in the SS A and B. Elementary analysis and calculation from the empirical formula $C_{36}H_{38}N_8O_9$ gave the following values: C = 59.08% (59.50%); H = 5.11% (5.27%); N = 15.80% (15.42%).

XVb. $N^\alpha$-Cbo-Pro-Tyr(OBzl)-Arg(NO₂)-pNA 1.25 g (2 mmoles) of compound XVa were deblocked according to Example 1, paragraph I (b). The resulting hydrobromide derivative was dissolved in 15 ml of DMF. After cooling 0.30 g (3 mmoles) of Et₃N and then 815 mg (2.2 mmoles) of CboPro-OpNP were added to the solution. The reaction mixture was further treated according to Example 1, paragraph I (b). After gel filtration on a column of "Sephadex LH-20" in MeOH 928 mg (56.3% of the theory) of the amorphous compound XVb were obtained. This compound was homogeneous according to TLC in the SS A and B. Elementary analysis and calculation from the empirical formula $C_{41}H_{45}N_9O_{10}$ gave the following values: C = 56.72% (56.42%); H = 6.09% (6.27%); N = 17.60% (17.42%).

XVc. $N^\alpha$-Bz-Pro-Tyr(OBzl)-Arg(NO₂)-pNA 824 mg (1 mmole) of compound XVb were deblocked according to Example 1, paragraph I (b). The resulting product was dissolved in 10 ml of DMF and 210 μl (1.5 mmoles) of Et₃N were added to the solution. After cooling 340 mg (1.5 mmoles) of Bz₂O were added to the solution. The reaction product was further treated according to Example 1, paragraph I (d). Purification: gel filtration on "Sephadex LH-20" in MeOH. Yield: 422 mg of amorphous substance (53.2% of the theory) which was homogeneous according to TLC in the SS A and B. Elementary analysis and calculation from the empirical formula $C_{40}H_{43}N_9O_9$ gave the following values: C = 60.92% (60.52%); H = 5.38% (5.46%); N = 16.19% (15.88%).

XV. $N^\alpha$-Bz-Pro-Tyr-Arg-pNA.HCl .HCl 412 mg (0.5 mmole) of compound XVc were reacted according to Example 1, paragraph I (e) to form compound XV. Purification: gel filtration on "Sephadex G-15" in 30% AcOH. Yield: 208 mg of freeze-dried amorphous powder (59.8% of the theory) which was homogeneous according to TLC in the SS C. Elementary analysis and calculation from the empirical formula $C_{33}H_{39}N_8O_7Cl$ gave the following values: C = 57.43% (57.01%); H = 5.78% (5.65%); N = 16.35% (16.12%); Cl = 4.98% (5.10%).

The amino acid analysis confirmed the presence of the expected amino acids in the correct proportions: Arg: 0.95 — Tyr: 1.00 — Pro: 0.98.

EXAMPLE 16

XVI. $N^\alpha$-Bz-Pro-Ph.Gly-Arg-pNA.HCl

XVIa. $N^\alpha$-Cbo-Ph.Gly-Arg(NO₂)-pNA 2.37 g (5 mmoles) of compound I (a) (cf. Example 1) were deblocked according to Example 1, paragraph I (b). The resulting hydrobromide derivative was dissolved in 30 ml of DMF. After cooling to −10° C 1.05 ml (7.5 mmoles) of Et₃N and then 2.32 g (5.71 mmoles) of Cbo-Ph.Gly-OpNP were added to the solution. The reaction mixture was further treated according to Example 1, paragraph I (b). After gel filtration on "Sephadex LH-20" in MeOH 2.62 g (86.4% of the theory) of the amorphous compound XVIa were obtained. This compound was homogeneous according to TLC in the SS A and B. Elementary analysis and calculation from the empirical formula $C_{28}H_{30}N_8O_8$ gave the following values: C = 55.10% (55.44%); H = 5.08% (4.99%); N = 18.81% (18.47%).

XVIb. $N^\alpha$-Cbo-Pro-Ph.Gly-Arg(NO₂)-pNA 1.22 g (2 mmoles) of compound XVIa were deblocked according to Example 1, paragraph I (b). The resulting hydrobromide derivative was dissolved in 15 ml of DMF. After cooling 300 mg (3 mmoles) of Et₃N and then 815 mg (2.2 mmoles) of CboPro-OpNP were added to the solution. The reaction mixture was further treated according to Example 1, paragraph I (b). After gel filtration on "Sephadex LH-20" in MeOH 1.17 g (83.1% of the theory) of the amorphous compound XVIb were obtained. This compound was homogeneous according to TLC in the SS A and B. Elementary analysis and calculation from the empirical formula $C_{33}H_{37}N_9O_9$ gave the following values: C = 56.08% (56.32%); H = 5.21% (5.30%); N = 18.02% (17.91%).

XVIc. $N^\alpha$-Bz-Pro-Ph.Gly-Arg(NO₂)-pNA 704 mg (1 mmole) of compound XVIb were deblocked according to Example 1, paragraph I (b). The resulting product was dissolved in 10 ml of DMF and 210 μl (1.5 mmoles) of Et₃N were added to the solution. After cooling 340 mg (1.5 mmoles) of Bz₂O were added. The reaction product was further treated according to Example 1, paragraph I (d). Purification: gel filtration on "Sephadex LH-20" in MeOH. Yield: 518 mg of amorphous substance (76.9% of the theory) which was homogeneous according to TLC in the SS A and B. Elementary analysis and calculation from the empirical formula $C_{32}H_{35}N_9O_8$ gave the following values: C = 56.85% (57.05%); H = 5.19% (5.24%); N = 18.96% (18.71%).

XVI. $N^\alpha$-Bz-Pro-Ph.Gly-Arg-pNA·HCl 337 mg (0.5 mmole) of compound XVIc were reacted according to Example 1, paragraph I (e), in order to form compound XVI. Purification: gel filtration on "Sephadex G-15" in 30% AcOH. Yield: 207 mg of freeze-dried amorphous powder (62.2% of the theory) which was homogeneous according to TLC in the SS C. Elementary analysis and calculation from the empirical formula $C_{32}H_{37}N_8O_6Cl$ gave the following values: C = 57.52% (57.78%); H = 5.73% (5.61%); N = 16.98% (16.85%); Cl = 5.25% (5.33%).

The amino acid analysis confirmed the presence of the expected amino acids in the correct proportions: Arg: 0.97 — Ph·Gly: 1.05 — Pro: 1.00.

EXAMPLE 17

XVII. $N^\alpha$-Bz-Pro-Phe-Arg-2-NA·HCl

XVIIa. $N^\alpha$-Cbo-Arg(NO₂)-2-NA 3.53 g (10 mmoles) of well dried Cbo-Arg(NO₂)-OH were dissolved in 150 ml of THF:DMF (3 : 1) in a moisture-free atmosphere. After cooling to −10° C 1.39 ml (10 mmoles) of Et₃N were added to the solution and then a solution of 1.35 g (10 mmoles) if isobutyl chloroformate in 20 ml of THF were added dropwise within 15 minutes, the temperature being maintained at −10° to −5° C. A solution of 1.72 g (12 mmoles) of β-naphthylamine in 15 ml of THF was then added dropwise to the thus obtained solution, the above mentioned temperature being maintained. The reaction mixture was further treated according to Example 1, paragraph I (a)-2. After gel filtration on "Sephadex LH-20" in MeOH 3.75 g of the crystalline compound XVIIa (78.4% of the theory) having a m.p. of 173°–174.5° C were obtained. This compound was homogeneous according to the TLC in the SS A and B. Elementary analysis and calculation from the empirical formula $C_{24}H_{26}N_6O_5$ gave the following values: C = 60.82% (60.24%); H = 5.63% (5.48%); N = 17.48% (16.72%).

XVIIb. N $^\alpha$ -Cbo-Phe-Arg($NO_2$)2-NA 2.87 g (6 mmoles) of compound XVIIa were deblocked according to Example 1, paragraph I (b). The resulting hydrobromide derivative was dissolved in 50 ml of DMF. After cooling to −10° C 1.25 ml (9 mmoles) of $Et_3N$ were added to the solution. The $Et_3N\cdot HBr$ which had formed was filtered off and washed with a small quantity of cold DMF. 2.78 g (6.6 mmoles) of Cbo-Phe-OpNP were added to the thus obtained DMF-solution. The reaction mixture was further treated according to Example 1, paragraph I (b). After gel filtration on "Sephadex LH20" in MeOH 3.23 g (86% of the theory) of the amorphous compound XVIIb were obtained. This compound was homogeneous according to TLC in the SS A and B. Elementary analysis and calculation from the empirical formula $C_{33}H_{35}N_7O_6$ gave the following values: C = 63.10% (63.35%); H = 5.54% (5.64%); N = 15.80% (15.67%).

XVIIc. N $^\alpha$ -Cbo-Pro-Phe-Arg($NO_2$)-2-NA 1.88 g (3 mmoles) of compound XVIIb were deblocked according to Example 1, paragraph I (b). The resulting product was dissolved in 20 ml of DMF. 0.63 ml (4.6 mmoles) of $Et_3N$ and then 1.22 g (3.3 mmoles) of Cbo-Pro-OpNP were then added to the solution. The reaction mixture was further treated according to Example 1, paragraph I (b). After gel filtration on "Sephadex LH-20" in MeOH 1.72 g (79.3% of the theory) of the amorphous compound XVIIc were obtained. This compound was homogeneous according to TLC in the SS A and B. Elementary analysis and calculation from the empirical formula $C_{38}H_{42}N_8O_7$ gave the following values: C = 62.93% (63.14%); H = 5.82% (5.86%); N = 15.75% (15.50%).

XVIId. N $^\alpha$ -Bz-Pro-Phe-Arg($NO_2$)-2-NA 1.08 g (1.5 mmoles) of compound XVIIc were deblocked according to Example 1, paragraph I (b). The resulting product was dissolved in 12 ml of DMF and 315 μl (2.25 mmoles) of $Et_3N$ were added to the solution. After cooling 510 mg (2.25 mmoles) of $Bz_2O$ were added to the solution. The reaction mixture was further treated according to Example 1, paragraph I (d). Purification: gel filtration on "Sephadex LH-20" in MeOH. Yield: 765 mg of amorphous substance (73.6% of the theory) which was homogeneous according to TLC in the SS A and B. Elementary analysis and calculation from the empirical formula $C_{37}H_{40}N_8O_6$ gave the following values: C = 63.88% (64.15%); H = 5.75% (5.82%); N = 16.49% (16.18%).

XVII. N $^\alpha$ -Bz-Pro-Phe-Arg-2-NA·HCl 693 mg (1 mmole) of compound XVIId were reacted according to Example 1, paragraph I (e), in order to form compound XVII. Purification: gel filtration on "Sephadex G-15" in 30% AcOH. Yield: 455 mg of freeze-dried amorphous powder (66.5% of the theory) which was homogeneous according to TLC in the SS C. Elementary analysis and calculation from the empirical formula $C_{37}H_{42}N_7O_4Cl$ gave the following values: C = 65.18% (64.95%); H = 6.13% (6.19%); N = 14.55% (14.33%); Cl = 5.09% (5.18%).

The amino acid analysis confirmed the presence of the expected amino acids in the correct proportions: Arg: 0.98 — Phe: 1,00 — Pro: 0.94.

EXAMPLE 18

XVIII. N $^\alpha$ -Bz-Pro-Phe-Arg-4-MeO-2-NA·HCl

XVIIIa. N $^\alpha$ -Cbo-Arg($NO_2$)-4-MeO-2-NA

A solution of 2.08 g (12 mmoles) of 4-methoxy-2-naphthylamine in 15 ml of THF (instead of β-naphthylamine) was added dropwise according to Example 17, paragraph XVIIa, to 3.53 g (10 mmoles) of Cbo-Arg($NO_2$)-OH. After gel filtration on "Sephadex LH-20" in MeOH 3.91 g of the amorphous compound XVIIIa (76.9% of the theory) were obtained. This compound was homogeneous according to TLC in the SS A and B. Elementary analysis and calculation from the empirical formula $C_{25}H_{28}N_6O_6$ gave the following values: C = 59.20% (59.05%); H = 5.41% (5.55%); N = 16.72% (16.53%).

XVIIIb. N $^\alpha$ -Cbo-Phe-Arg($NO_2$)-4-MeO-2-NA 2.55 g (5 mmoles) of compound XVIIIa were deblocked according to Example 1, paragraph I (b). The resulting hydrobromide derivative was dissolved in 50 ml of DMF. After cooling to −10° C 1.05 ml (7.5 mmoles) of $Et_3N$ and then 2.31 g (5.5 mmoles) of Cbo-Phe-OpNP were added to the solution. The reaction mixture was further treated according to Example 1, paragraph I (b). After gel filtration on "Sephadex LH-20" in MeOH 2.55 g (77.8% of the theory) of the amorphous compound XVIIIb were obtained. This compound was homogeneous according to TLC in the SS A and B. Elementary analysis and calculation from the empirical formula $C_{34}H_{37}N_7O_7$ gave the following values: C = 61.95% (62.28%); H = 5.62% (5.69%); N = 15.11% (14.95%).

XVIIIc. N $^\alpha$ -Cbo-Pro-Phe-Arg($NO_2$)-4-MeO-2-NA 1.97 g (3 mmoles) of compound XVIIIb were deblocked according to Example 1, paragraph I (b). The resulting product was dissolved in 20 ml of DMF. 0.63 ml (4.6 mmoles) of $Et_3N$ and then 1.22 g (3.3 mmoles) of Cbo-Pro-OpNP were added to the solution. The reaction mixture was further treated according to Example 1, paragraph I (b). After gel filtration on "Sephadex LH-20" in MeOH 1.54 g (68.3 % of the theory) of the amorphous compound XVIIIc were obtained. This compound was homogeneous according to TLC in the SS A and B. Elementary analysis and calculation from the empirical formula $C_{39}H_{44}N_8O_8$ gave the following values: C = 62.05% (62.22%); H = 5.91% (5.89%); N = 15.08% (14.89%).

XVIIId. N$^\alpha$-Bz-Pro-Phe-Arg(NO$_2$)-4-MeO-2-NA 1.13 g (1.5 mmoles) of compound XVIIIc were deblocked according to Example 1, paragraph I (b). The resulting product was dissolved in 12 ml of DMF and 315 μl (2.25 mmoles) of Et$_3$N were added to the solution. After cooling 510 mg (2.25 mmoles) of Bz$_2$O were added to the solution. The reaction mixture was further treated according to Example 1, paragraph I (d). Purification: gel filtration on "Sephadex LH-20" in MeOH. Yield: 780 mg of amorphous substance (71.9% of the theory) which was homogeneous according to TLC in the SS A and B. Elementary analysis and calculation from the empirical formula C$_{38}$H$_{42}$N$_8$O$_7$ gave the following values: C = 63.48% (63.14%); H = 5.75% (5.86%); N = 15.78% (15.50%).

XVIII. N$^\alpha$-Bz-Pro-Phe-Arg-4-MeO-2NA·HCl 723 mg (1 mmole) of compound XVIIId were reacted according to Example 1, paragraph I (e), in order to form compound XVIII. Purification: gel filtration on "Sephadex G-15" in 30% AcOH. Yield: 488 mg of freeze-dried amorphous powder (68.3% of the theory) which was homogeneous according to TLC in the SS C. Elementary analysis and calculation from the empirical formula C$_{38}$H$_{44}$N$_7$O$_5$Cl gave the following values: C = 63.58% (63.90%); H = 6.15% (6.21%); N = 14.03% (13.73%); Cl = 4.88% (4.96%).

The amino acid analysis confirmed the presence of the expected amino acids in the correct proportions: Arg: 0.93 — Phe: 1.00 — Pro: 0.94.

The substrates according to the invention, e.g. the substrate prepared according to Example 1, i.e. N$^\alpha$-Bz-Pro-Phe-Arg-pNA·HCl, were used for the quantitative determination of various enzymes in blood plasma. The determination was carried out by taking advantage of the fact that the split product NH$_2$-R$^2$ formed by enzymatic hydrolysis of the substrate has a UV spectrum which differs from that of the substrate and is shifted toward higher wave lengths. Thus, N$^\alpha$-Bz-Pro-Phe-Arg-pNA·HCl has an absorption maximum at 302 nm (nanometer) and a molecular extinction coefficient of 12,950. The absorption of the substrate is practically nil at 405 nm. p-Nitroaniline (pNA), i.e. the split product NH$_2$—R$^2$ formed by the enzymatic hydrolysis of the substrate, has an absorption maximum at 380 nm and a molecular extinction coefficient of 13,200. At 405 nm the extinction coefficient is but moderately reduced, i.e. to 9.650.

The degree of the enzymatic hydrolysis of the substrate, which is proportional to the quantity of p-nitroaniline formed, can be easily determined by spectrophotometric measurement at 405 nm. The presence of an excess of substrate exerts no disturbing effect on the measurement at 405 nm. The conditions are practically the same for the other substrates carrying a p-nitroanilino group as a chromogenic group. The spectrophotometric measurement was, therefore, carried out in all cases at 405 nm.

The enzymatic hydrolysis reaction can be represented by the following scheme:

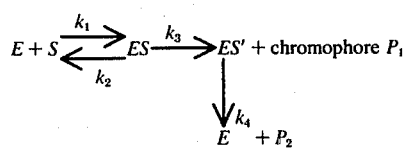

$E$ = enzyme
$S$ = substrate
$\underline{ES}$ = enzyme-substrate complex
$P_1$ and $P_2$ = products
$k_1$, $k_2$, $k_3$ and $k_4$ = rate constants
Dissociation constant for $ES = k_2/k_1 = K_m$ (Michaelis constant)
If $[S] >> [E]$ and $k_4 << k_3$, the following is true:

$$K_m = \frac{([E] - [ES]) \cdot [S]}{[ES]} \quad (1)$$

The rate constant at which chromophore P$_1$ is formed is
$v = k_3 \cdot [ES]$ $$v = \frac{k_3 \cdot [E] \cdot [S]}{K_m + [S]} \quad (2)$$

If E is completely bound to S, then $[ES] = [E]$ and $$v = v_{max} = k_3 \cdot [E] \quad (3)$$

Lineweaver-Burk equation:

$$\frac{1}{v} = \frac{K_m}{v_{max}} \cdot \frac{1}{[S]} + \frac{1}{v_{max}} \quad (4)$$

As is evident from equation (2) constants $K_m$ and $k_3$ determine the activity of the enzyme substrate for a given enzyme. For determining these constants the following procedure is followed:

The enzyme and the substrate are mixed in a buffer solution, and the reaction is followed spectrophotometrically for 2 to 30 minutes. The concentration of substrate [S] is varied, whereas the enzyme concentration [E] is kept constant. If the extinction (OD) (= optical density) is plotted in a co-ordinate system as a function of time, a curve is obtained the tangent of which (difference in extinction per minute, Δ OD/minute, from which the quantity in μmoles of pNA/min ($v$) can be calculated) at time zero corresponds to the ideal course of the hydrolysis. By means of this tangent the initial rate of the hydrolysis can be determined.

If $1/v$ is plotted against $1/[S]$, a Lineweaver-Burk diagram (cf. "Kurzes Lehrbuch der Biochemie" by P. KARSON, Georg Thieme-Verlag, Stuttgart, 1967, p. 70) is obtained from which $v_{max}$ and $K_m$ can be determined graphically.

$K_m$ and $k_3 = v_{max}/E$ were determined with N$^\alpha$-Bz-Pro-Phe-Arg-pNA·HCl (i.e. the substrate prepared according to Example 1) for plasma kallikrein, trypsin, plasmin and thrombin. The results are summarized in Table I.

TABLE I

| Enzyme activity measured with Nα-Bz-Pro-Phe-Arg-pNA.HCl | | | |
|---|---|---|---|
| Enzyme | $K_m$ moles/liter | $v_{max}$ μmoles/min./U[5] | relation between substrate units and common units |
| Plasma kallikrein | $2.82 \cdot 10^{-4}$ | $950 \cdot 10^{-3}$ | 1 U = 4.8 BAEE U[1] |
| Plasmin | $1.4 \cdot 10^{-4}$ | $32 \cdot 10^{-3}$ | 1 U = 518 C U[4] |
| Trypsin | $1.7 \cdot 10^{-4}$ | $2.22 \cdot 10^{-3}$ | 1 U = 12000 NF[2] |
| Thrombin | $1.6 \cdot 10^{-4}$ | $0.14 \cdot 10^{-3}$ | 1 U = 117600 NIH[3] |

[1] One plasma kallikrein BAEE-unit is the quantity of enzyme which hydrolyzes 1 μmole of benzoyl-L-arginine ethyl ester per minute under standard conditions.

[2] One trypsin NF-unit is the quantity of enzyme which causes a change in the absorption of ΔOD = 0.003 per minute, measured on benzoyl-L-arginine ethyl ester under standard conditions (cf. "The National Formulary XII", edited by "The American Pharmaceutical Association", Washington, D.C., 1965, p. 417 and 418).

[3] The thrombin NIH-unit is the unit defined by the "US National Institute of Health".

[4] The plasmin C-unit is the casein unit, measured on casein under standard conditions.

[5] One enzyme unit is the quantity of enzyme which hydrolyzes 1 μmole of substrate per minute at substrate saturation.

In the third column of Table I the enzyme units determined with the substrate according to Example 1 are compared with the commonly used enzyme units.

The figures of the drawings attached to the specification have the following meaning:

Figure 1:
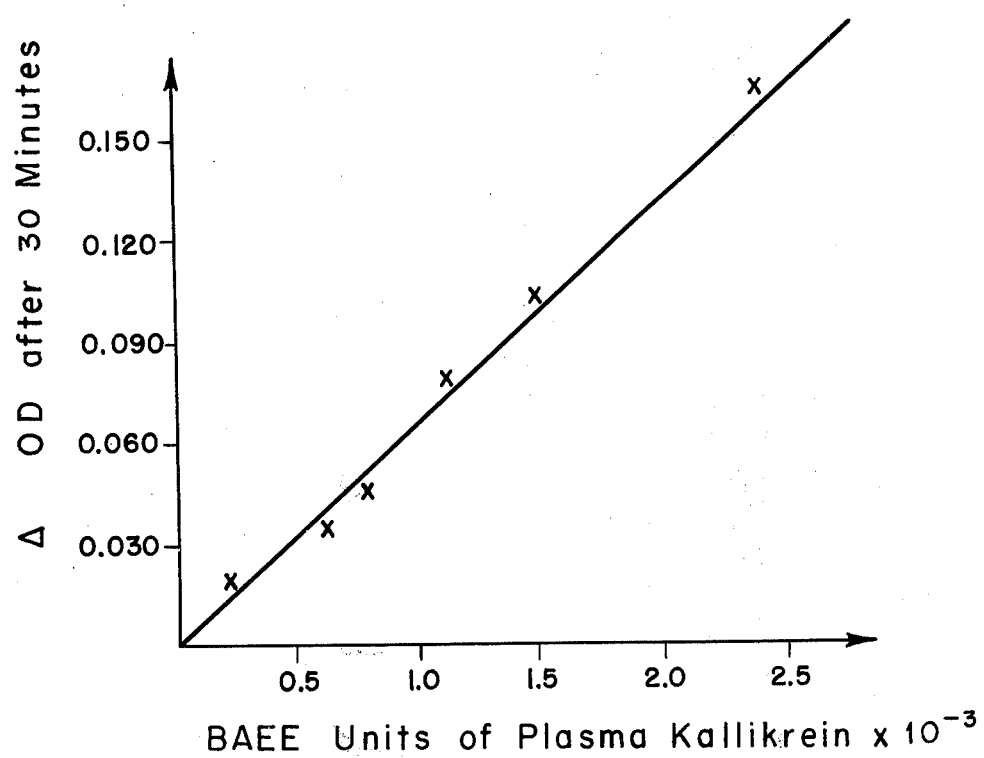
FIG. 1 is a graph in which the change in the optical density Δ OD caused by the hydrolytic activity of plasma kallikrein on the substrate of Example 1 within 30 minutes is plotted against the quantity of plasma kallikrein in a co-ordinate system.

The dose/activity curve of FIG. 1 was determined at various plasma kallikrein concentrations and at a constant substrate concentration. The measurements were carried out at 25° C and pH 8.2 in the presence of a tris-imidazole buffer having an ionic strength of 0.15.

Figure 2:
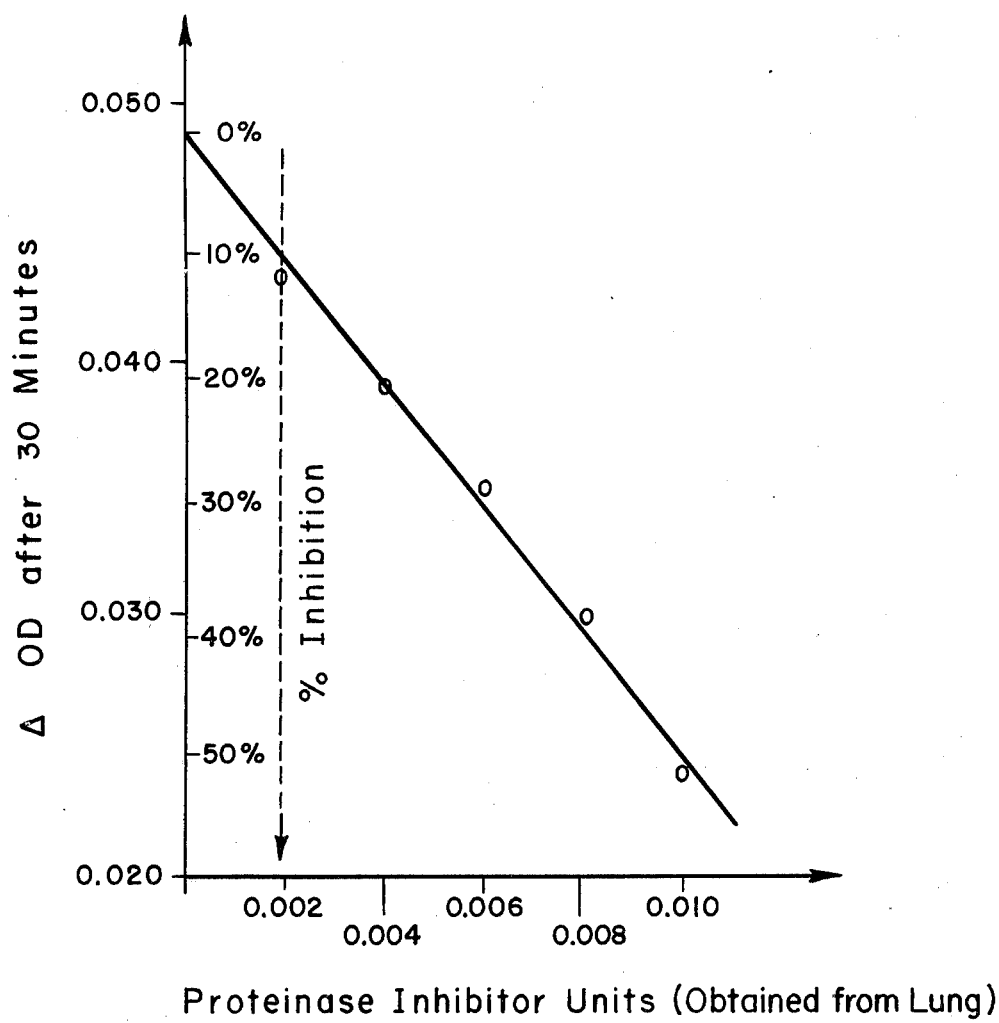
FIG. 2 is a graph in which the decrease of the optical density Δ OD is plotted against the quantity of kallikrein inhibitor present in an aqueous buffered medium at a constant concentration of plasma kallikrein and substrate according to Example 1.

The measurements the results of which are shown in FIG. 2 were carried out as follows: 0.25 ml of plasma kallikrein solution (0.0275 BAEE units per ml) was added to 2.0 ml of tris-imidazole buffer (pH 8.2, ionic strength: 0.15). Then 0.25 ml of kallikrein inhibitor solution (protease inhibitor obtained from lungs) was added. The mixture was incubated for exactly 10 minutes at 25° C. Thereafter, 0.5 ml of aqueous substrate solution (0.679 mg of the substrate of Example 1 per ml) was added. The mixture was incubated for 30 minutes at 25° C. The reaction was interrupted by the addition of 1.0 ml of 2 N acetic acid. Then the absorption was measured by means of a spectrophotometer at 405 nm.

Figure 3:
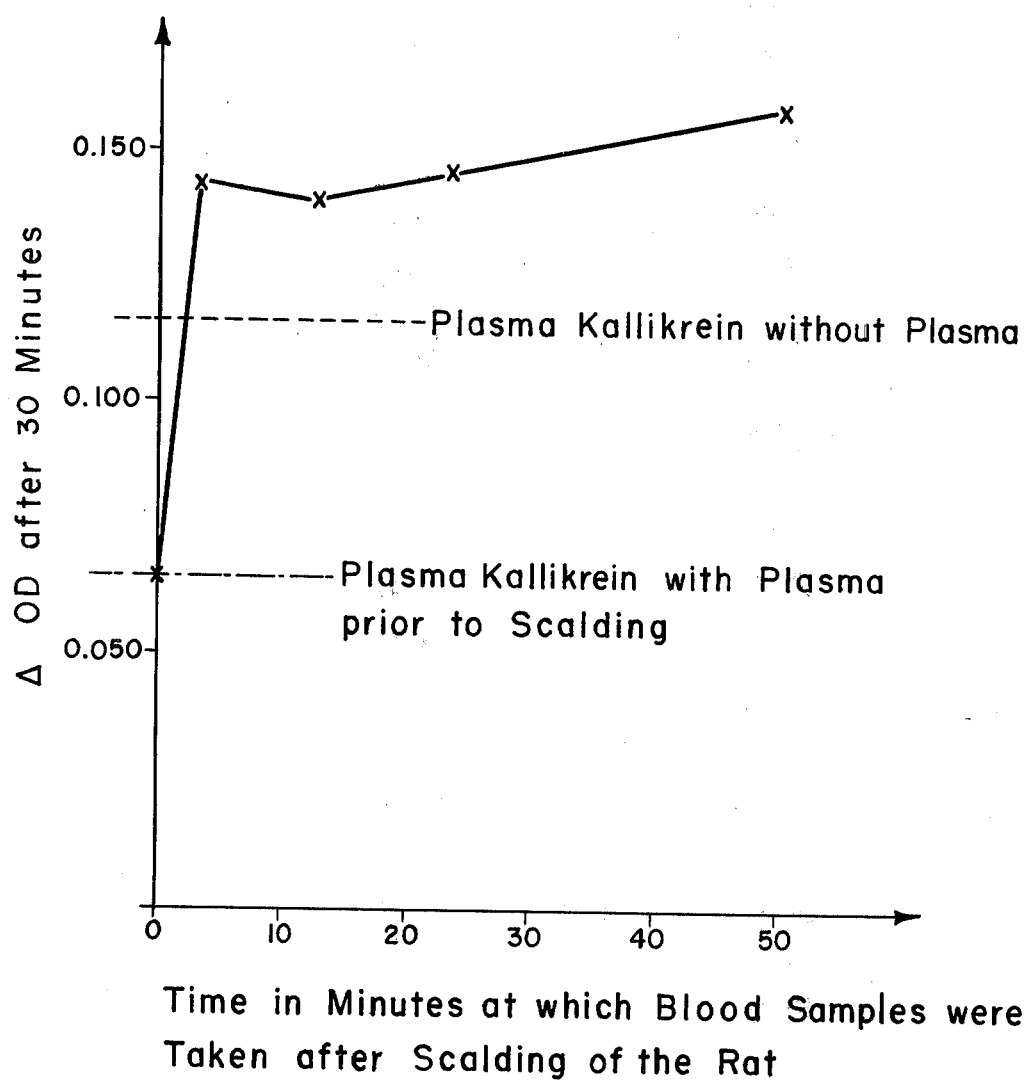
FIG. 3 is a graph in which the inhibiting capacity or induced proteolytic activity of rat plasma after inducement of a shock or stress is plotted against time at a constant concentration of substrate obtained according to Example 1.

The measurements the results of which are shown in FIG. 3 were carried out as follows: In order to induce a shock or stress in a rat its right hind-leg was scalded by immersing it for 10 seconds in water heated to 80° C. Then blood was taken from the rat. 0.25 ml of plasma kallikrein solution (0.022 BAEE units) was added to 2.0 ml of tris-imidazole buffer (pH 8.2, ionic strength: 0.15). Then 0.01 ml of the rat blood plasma was added to the mixture which was incubated for 5 minutes at 25° C. Subsequently 0.5 ml of aqueous substrate solution (0.679 mg of the substrate of Example 1 per ml) was added to the mixture which was incubated for exactly 30 minutes at 25° C. The increase in the absorption was measured spectrophotometrically at 405 nm. The measurement was also carried out on a blank sample containing only plasma kallikrein.

From Table I it can be seen that the substrate of the invention has a much higher specificity for plasma kallikrein than for plasmin, trypsin, and thrombin. $v_{max}$ is substantially higher for plasma kallikrein than for the other enzymes as is evidenced by the fact that the substrate is hydrolyzed much more quickly by plasma kallikrein than by the other enzymes. Hence it is possible to determine accurately minute quantities of plasma kallikrein and of its inhibitors. This is very important in clinical work where often only very small quantities of plasma samples are available.

From Table I it can further be seen that thrombin does not disturb the determination of plasma kallikrein and its inhibitors.

A further advantage of the substrate of the invention resides in the fact that the enzymatic hydrolysis caused by plasma kallikrein follows the law of Michaelis-Menton and that it is, therefore, possible to determine the kinetic constants $K_m$ and $v_{max}$.

From FIG. 1 and 2 it can be seen how accurate and sensitive the determination of plasma kallikrein and its inhibitors is. This constitutes an important advantage insofar as it is possible to control continuously the therapy of shock or stress conditions in humans by protease-inhibitors and to dose accurately their administration.

FIG. 3 shows how a shock or stress condition in which the plasma kallikrein system is activated can be detected by means of the substrate of the invention. The activation of the plasma kallikrein system, which is characteristic of such shock or stress conditions, can be determined accurately by means of the said substrate.

The split product $NH_2$—$R^2$ can be diazotized and coupled with a coupling component prior to the photometric determination.

TABLE II

Activity of plasma kallikrein and human plasmin, measured with the substrates of the invention at constant substrate and enzyme concentrations

| Substrate | Quantity in nm of p-nitroaniline (pNA), β-naphthyl-amine (2-NA) or 4-methoxy-β-naphthylamine (4-MeO-2-NA) released within 1 minute by 1 BAEE unit of plasma kallikrein or one C unit of human plasmin | |
|---|---|---|
| | Plasma kallikrein | human plasmin |
| Ie | 135.5 nm pNA | 152.0 nm pNA |
| II | 28.6 nm pNA | 16.2 nm pNA |
| III | 42.3 nm pNA | 49.1 nm pNA |
| IV | 108.3 nm pNA | 100.0 nm pNA |
| V | 154.7 nm pNA | 158.0 nm pNA |
| VI | 78.4 nm pNA | 142.0 nm pNA |
| VII | 256.0 nm pNA | 144.0 nm pNA |
| VIII | 59.7 nm pNA | 256.0 nm pNA |
| IX | 65.1 nm pNA | 600.0 nm pNA |
| X | 88.5 nm pNA | 80.2 nm pNA |
| XI | 72.1 nm pNA | 230.0 nm pNA |
| XII | 49.2 nm pNA | 196.0 nm pNA |
| XIII | 109.9 nm pNA | 176.1 nm pNA |
| XIV | 64.5 nm pNA | 116.0 nm pNA |
| XV | 71.0 nm pNA | 73.8 nm pNA |
| XVI | 9.1 nm pNA | 16.2 nm pNA |
| XVII | 44.1 nm 2-NA | 95.4 nm 2-NA |
| XVIII | 39.8 nm 4-MeO-2-NA | 79.7 nm 4-MeO-2-NA |

TABLE III

Activity of papain and prothrombin activator, measured by means of substrates of the invention at a constant substrate concentration

| Substrate | Quantity in nm of p-nitroaniline (pNA) released within 1 minute by 0.1 milli-Anson unit[3] of papain and 10 μg of a pure fraction of the prothrombin activator from venom of the snake Echis carinatus | |
|---|---|---|
| | Prothrombin activator[2] | Papain[1] |
| I | 13.1 nm pNA | |
| VII | | 24.9 nm pNA |

[1]Papain is a cysteine-protease isolated from the latex of the green carica papaya fruit.
[2]The prothrombin activator is a serine-protease which was isolated from the venom of the snake Echis carinatus.
[3]One Anson unit is the enzyme quantity which releases 1 mmole of folin-positive amino acids (calculated as tyrosine) in 1 minute (cf. Art. No. 7144 published by the firm MERCK).

I claim:
1. A chromogenic or fluorescent substrate for the quantitative determination of proteolytic enzymes of class E.C. 3.4.4., which split peptide chains on the carboxyl side of arginine and of lysine, except thrombin and thrombin-like enzymes, in human and mammal body fluids and in vegetable and animal cell extracts and in glandular venoms of cold-blooded animals, which essentially consists of a compound having the following formula:

$$R^1 — Pro — X — Y — NH — R^2 \qquad I$$

wherein $R^1$ represents hydrogen, or an acyl or sulfonyl group, $R^2$ represents an aromatic hydrocarbon group which may carry substituents, X represents a phenylalanyl, β-cyclohexylalanyl, phenylglycyl or tyrosyl group and Y represents a protonized arginyl or lysyl group, —NH—$R^2$ being a chromogenic or fluorescent group, and which, when subjected to the proteolytic action of the enzymes, yields a split product of formula $NH_2$—$R^2$ the quantity of which is measurable by photometric, spectrophotometric or fluorescence-photometric methods.

2. The substrate according to claim 1 in which the acyl group $R^1$ has the following partial formula $R^3$ — CO — (II) wherein $R^3$ represents a. an aliphatic hydrocarbon radical which comprises from 1 to 17 carbon atoms and which may carry an amino group in the ω-position;
b. an araliphatic hydrocarbon radical which comprises from 1 17 carbon atoms and the aryl component of which may carry an amino group;
c. a cycloaliphatic hydrocarbon radical which may carry an amino group or an aminomethyl group;
d. an aromatic hydrocarbon radical which may carry an alkyl, amino or aminoalkyl group; or
e. a benzyloxy group.

3. The substrate according to claim 1 in which the sulfonyl group $R^1$ is a benzenesulfonyl or p-toluenesulfonyl group.

4. The substrate according to claim 1 in which $R^2$ is a p-nitrophenyl, β-naphthyl or 4-methoxy-β-naphthyl group.

5. The substrate according to claim 1 which is protonized with a mineral acid such as HCl, HBr, $H_2SO_4$ or $H_3PO_4$, or an organic acid such as formic acid, oxalic acid or tartaric acid.

6. N$^\alpha$-3-Phenylpropionyl-Pro-Phe-Arg-pNA-hydrochloride.
7. N$^\alpha$-Cyclohexylcarbonyl-Pro-Phe-Arg-pNA-hydrochloride.
8. N$^\alpha$-Benzoyl-Pro-Phe-Arg-pNA-hydrochloride.
9. N$^\alpha$-Cbo-Pro-Phe-Arg-pNA-hydrochloride.
10. N$^\alpha$-Caproyl-Pro-Phe-Arg-pNA-hydrochloride.
11. A process for the quantitative determination of proteolytic enzymes of class E.C. 3.4.4., which split peptide chains on the carboxyl side of arginine as well as of lysine, except thrombin and thrombin-like enzymes, in human and mammal body fluids as well as in vegetable and animal cell extracts and in glandular venoms of cold-blooded animals, which comprises reacting the said body fluids, cell extracts or glandular venoms with a substrate according to claim 1 and measuring by means of photometric, spectrophotometric or fluorescence-photometric methods the quantity of the product $NH_2$—$R^2$ split off from the substrate as a result of the proteolytic action of the enzymes on the substrate.

12. The process according to claim 11 as applied to the quantitative determination of plasma pre-kallikrein and its activators, plasma kallikrein and its inhibitors, papain and prothrombin activators.

* * * * *

UNITED STATES PATENT AND TRADEMARK OFFICE
CERTIFICATE OF CORRECTION

PATENT NO. : 4,016,042
DATED : April 5, 1977
INVENTOR(S) : Lars Gundro Svendsen

It is certified that error appears in the above-identified patent and that said Letters Patent are hereby corrected as shown below:

| | |
|---|---|
| Column 1, Line 40 | Reads "Nα-L" should read --Nα-benzoyl-L-- |
| Column 4, Line 7 | Reads "step-wide" should read --step-wise-- |
| Column 5, Line 70 | Reads "potions" should read --portions-- |
| Column 6, Line 53 | Reads "in dryness" should read --to dryness-- |
| Column 8, Line 8-9 | Reads "To filtrate" should read --To the filtrate-- |
| Column 12, Line 20 | Reads "69.2%" should read --68.2%-- |
| Column 13, Line 24 | Reads "NA.HCl HCl" should read --NA.HCl-- |
| Column 13, Line 52 | Reads "d(1.25 mmoles)" should read --(1.25 mmoles)-- |
| Column 17, Line 47 | Reads "pNA HCl.HCl" should read --pNA.HCl-- |

UNITED STATES PATENT OFFICE
CERTIFICATE OF CORRECTION

Patent No. 4,016,042     Dated April 5, 1977

Inventor(s) Lars Gundro Svendsen

It is certified that error appears in the above-identified patent and that said Letters Patent are hereby corrected as shown below:

Column 23, Table 1, lines 7-8 reads "1 U=4.8 BAEE $U_-^1$)" should read -- 1 U=4.8 BAEE-$U^1$) --

Signed and Sealed this

Sixth Day of September 1977

[SEAL]

Attest:

RUTH C. MASON
*Attesting Officer*

LUTRELLE F. PARKER
*Acting Commissioner of Patents and Trademarks*